United States Patent
Nemeth et al.

(10) Patent No.: US 6,191,323 B1
(45) Date of Patent: Feb. 20, 2001

(54) PROCESS FOR THE REDUCTION OF KETONES AND ALDEHYDES TO ALCOHOLS USING A TIN SUBSTITUTED ZEOLITE BETA

(75) Inventors: Laszlo T. Nemeth, Palatine, IL (US); Avelino Corma Canos; Susana Valencia Valencia, both of Valencia (ES); Jaime G. Moscoso, Mt. Prospect, IL (US); Marcelo Eduardo Domine, Valencia (ES)

(73) Assignee: UOP LLC, Des Plaines, IL (US)

( * ) Notice: Under 35 U.S.C. 154(b), the term of this patent shall be extended for 0 days.

(21) Appl. No.: 09/557,300

(22) Filed: Apr. 25, 2000

(51) Int. Cl.$^7$ ............ C07C 29/14; C07C 27/04; C01B 33/20; B01J 29/04
(52) U.S. Cl. ............ 568/881; 568/772; 568/885; 423/326; 423/705; 423/713; 423/714; 423/DIG. 27; 502/85
(58) Field of Search ............ 568/772, 881, 568/885; 423/713, 714, 705, 326, DIG. 27; 502/85

(56) References Cited

U.S. PATENT DOCUMENTS 5,354,915 * 10/1994 Reichle ............ 568/881
6,117,411 * 9/2000 Takewaki et al. ............ 423/705

OTHER PUBLICATIONS

*Chem. Commun.*, 1998, pp. 1811–1812, R. Anwander, C. Palmm, G. Gerstberger, O. Groeger and G. Engelhardt, Enhanced catalytic activity of MCM–41–grafted aluminum isopropoxide in MPV reductions.

R. Anwander and C. Palm, *Studies in Surface Science and Catalysis*, 1998, 117, pp. 413–420.

M.A. Aramendia, et al, *Catalysis Letters* 58 (1999) 53–58.

J.C.van der Waal, *Topics in Catalysis* 4 (1997) 261–268.

* cited by examiner

*Primary Examiner*—Porfirio Nazario-Gonzalez
(74) *Attorney, Agent, or Firm*—John G. Tolomei; Frank S. Molinaro

(57) ABSTRACT

A process for the reduction of ketones or aldehydes to alcohols has been developed. The process involves contacting the ketone or aldehyde with a primary or secondary alcohol and a catalyst at reduction conditions. The catalyst is a molecular sieve having the empirical formula:

$$(M_w Sn_x Ti_y Si_{1-x-y-z} Ge_z)O_2$$

where M is a trivalent metal such as aluminum or boron. These molecular sieves have a microporous three dimensional framework structure of at least $SiO_2$ and $SnO_2$ tetrahedral units, a crystallographically regular pore system and the characteristic x-ray diffraction pattern of zeolite beta.

15 Claims, No Drawings

PROCESS FOR THE REDUCTION OF KETONES AND ALDEHYDES TO ALCOHOLS USING A TIN SUBSTITUTED ZEOLITE BETA

FIELD OF THE INVENTION

This invention relates to a process for the reduction of ketones or aldehydes to alcohols. The process involves contacting the ketone or aldehyde with a secondary or primary alcohol and a catalyst which comprises a tin substituted zeolite beta at reduction conditions to form the corresponding alcohol.

BACKGROUND OF THE INVENTION

There is an increasing demand for organic compounds containing oxygen in the structure, e.g., ketones, aldehydes, alcohols, etc. and therefore, a demand for processes which are more efficient, selective and environmentally friendly. Since alcohols is one family of desired organic compounds, one selective reaction route is the Meerwein-Pondorf-Verley reduction of aldehydes and ketones and the Oppenauer oxidation of alcohols denoted as MPVO. The MPVO reactions do not reduce C=C double bonds nor C-halogen bonds and can be carried out under mild conditions. In MPV reduction a secondary alcohols is the reductant whereas in Oppenauer oxidations, a ketone is the oxidant.

The art discloses a number of references which address either the mechanism of the MPVO reaction or various catalysts for the reaction. For example, R. Anwander et al., in *Chem. Communic.* (1998) 1811 disclose a catalyst for MPV reduction which is an aluminum isopropoxide grafted onto purely siliceous MCM-41. R. Anwander and C. Palm in *Studies in Surface Science and Catalysis,* vol. 117; 413, L. Bonneviot, F. Beland, C. Danumah, S. Giasson and S. Kaliaguine, editors, (1998) Elsevier Science Press disclose grafting lanthanide alkoxide onto MCM-41; M. A. Aramendia et al. in *Catalysis Letters,* discloses the use of magnesium phosphates to catalyze the MPVO reaction. J. C. van der Waal et al. in *Topics in Catalysis,* 4 (1997), 261–268 (and references therein) disclose that zeolite beta and titanium containing beta can catalyze the MPVO reaction.

In contrast to the above art, applicants have carried out the MPVO reaction using a tin substituted molecular sieve which has the formula on an anhydrous basis of:

$$(M_w Sn_x Ti_y Si_{1-x-y-z} Ge_z)O_2$$

M is a metal having a +3 valence (trivalent metal) such as aluminum or boron, "w" has a value of about zero to about 2x, "x" can be from about 0.001 to about 0.1 while "y" and "z" have respectively values of zero to about 0.1 and 0 to about 0.08. As will be shown in detail in the examples, a tin containing zeolite beta catalyst is able to convert cyclohexanone to cyclohexanol using isopropanol or 2-butanol as the reductant. The tin-beta catalyst also has better activity and selectivity than zeolite beta or titanium zeolite beta.

SUMMARY OF THE INVENTION

One embodiment of this invention comprises a process for the reduction of organic oxygenates selected from the group consisting of ketones, aldehydes and mixtures thereof comprising contacting the oxygenate with a secondary or primary alcohol and a catalyst at reduction conditions to reduce the oxygenate to its corresponding alcohol, the catalyst comprising a molecular sieve having an empirical formula on a calcined and anhydrous basis of:

$$(M_w Sn_x Ti_y Si_{1-x-y-z} Ge_z)O_2$$

where M is a metal having a +3 valence, "w" is the mole fraction of M and varies from zero to about 2x, "x" is the mole fraction of tin and varies from about 0.001 to about 0.1, "y" is the mole fraction of titanium and varies from zero to about 0.1 and "z" is the mole fraction of germanium and varies from zero to less than about 0.08 and characterized in that the composition has the characteristic x-ray diffraction pattern of zeolite beta, and when "w", "y" and "z" are all zero, then the molecular sieve is amorphous with short range order or has the charateristic x-ray diffraction pattern of zeolite beta.

This and other objects and embodiments of the invention will become more apparent after a detailed description of the invention.

DETAILED DESCRIPTION OF THE INVENTION

As stated, the present application deals with a process for practicing the MPVO reaction. One essential part of this process is a catalyst which comprises a tin containing molecular sieve having the characteristic x-ray diffraction pattern of zeolite beta and an empirical formula on a calcined and anhydrous basis of:

$$(M_w Sn_x Ti_y Si_{1-x-y-z} Ge_z)O_2$$

"x" is the mole fraction of tin and varies from about 0.001 to about 0.1, "y" is the mole fraction of titanium and varies from zero to about 0.1 and "z" is the mole fraction of germanium and varies from zero to less than about 0.08. When "w", "y" and "z" are all zero, the molecular sieve can be amorphous with short range order or have the characteristic x-ray diffraction pattern of zeolite beta. The M metals which can be used include but are not limited to aluminum, boron, gallium, and iron; and "w" is the mole fraction of M and varies from 0 to about 2x. These molecular sieves have a microporous three dimensional framework structure of at least $SiO_2$ and $SnO_2$ tetrahedral units, and a crystallographically regular pore system.

These molecular sieves are prepared using a hydrothermal crystallization process in which a reaction mixture is prepared by combining reactive sources of tin, silicon, an organic templating agent, optionally germanium, optionally titanium, optionally a M metal, a fluoride or hydroxide source, optionally hydrogen peroxide and water. The sources of silicon include but are not limited to colloidal silica, amorphous silica, fumed silica, silica gel and tetraalkylorthosilicate. Sources of tin include but are not limited to tin halides, tin alkoxides, tin oxide, metallic tin, alkaline and alkaline earth stannates and alkyl tin compounds. A preferred source is tin tetrachloride. Examples of tin alkoxides include tin butoxide, tin ethoxide and tin propoxide. The organic templating agents include, without limitation, tetraalkylammonium ions such as tetraethylammonium ions, aza-polycyclic compounds such as 1,4-diazabicyclo 2,2,2, octane; dialkyldibenzylammonium ions such as dimethyldibenzyl ammonium ion and bis-piperidinium ions such as 4,4' trimethylene bis (N-benzyl N-methyl piperidinium) ion. These ions may be added as the hydroxide or halide compounds. Germanium sources include germanium halides, germanium alkoxides and germanium oxides. Titanium sources include titanium alkoxides and titanium halides. Preferred titanium alkoxides are titanium tetraethoxide, titanium isopropoxide and titanium tetrabutoxide. When M is Al, the sources of aluminum include but are not limited to alumina, aluminum oxides, such as pseudo-boehmite, aluminum alkoxides such as aluminum isopropoxide, sodium aluminate and aluminum trichloride, with pseudo-boehmite and aluminum alkoxides being preferred. Sources of boron, gallium and iron include oxides, hydroxides, alkoxides, nitrates, sulfates, halides, carboxylates and mixtures thereof. Representative compounds include, without limitation, boron alkoxides, gallium alkoxides, iron (II) acetate, etc.

The reaction mixture will also contain either a fluoride source such as hydrofluoric acid or ammonium fluoride or a hydroxide source such as sodium hydroxide or potassium hydroxide. The hydroxide source may also be added by using the hydroxide compound of the templating agent. Water is also added to the mixture and optionally hydrogen peroxide.

Generally, the hydrothermal process used to prepare the tin containing molecular sieves involves forming a reaction mixture, using the sources stated above, which is expressed by the formula:

$$SiO_2:kM_2O_3:aR_2O:bSnO_2:cGeO_2:dTiO_2:eF:fH_2O_2:gH_2O$$

where "k" has a value from zero to about 0.1, "a" has a value from about 0.06 to about 0.5, "b" has a value from about 0.001 to about 0.1, "c" has a value from zero to about 0.08, "d" has a value from 0 to about 0.1, "e" has a value from about 0.1 to about 2, "f" has a value from zero to about 0.5 and "g" has a value from about 4 to about 50. The reaction mixture is prepared by mixing the desired sources of tin, silicon, optionally titanium, optionally germanium, optionally a M metal, an organic templating agent, water, optionally hydrogen peroxide and a fluoride or hydroxide source in any order to give the desired mixture. It is also necessary that the pH of the mixture be in the range of about 6 to about 12 and preferably in the range of about 7.5 to about 9.5. If necessary the pH of the mixture can be adjusted by adding HF, NH$_4$F, NaOH, KOH, etc. Hydrogen peroxide may be added in order to form a complex with titanium and maintain it in solution.

Having formed the reaction mixture, it is next reacted at a temperature of about 90° C. to about 200° C. and preferably 120° C. to about 180° C. for a time of about 2 days to about 50 days and preferably from about 10 days to about 25 days in a sealed reaction vessel under autogenous pressure. After the allotted time, the mixture is filtered to isolate the solid product which is washed with deionized water and dried in air.

In order to promote crystallization (of the beta structure), it is preferred to add zeolite beta crystals as seeds to the reaction mixture. These crystals can be added as a dry solid, a suspension in an appropriate liquid, e.g., water, alcohol or a preorganized gel, i.e., a gel which contains nuclei. A preferred zeolite beta seed is one prepared according to the teachings of Spanish Patent Application No. P9501552.

The isolated molecular sieve is characterized in that it has the x-ray diffraction pattern characteristic of zeolite beta which includes at least the peaks and intensities presented in Table A. The intensity presented in Table A is a relative intensity which is obtained by relating the intensity of each peak (I) to the strongest line (I$_o$). The intensity is given by the equation 100×I/I$_o$ and are represented by vs, s, m and w, where these are defined as: vs=80–100; s=60–80; m=15–60 and w=0–15.

TABLE A

| 2 θ   | d (Å) | Relative Intensity |
|-------|-------|--------------------|
| 7.22  | 12.23 | m                  |
| 7.76  | 11.38 | s                  |
| 21.54 | 4.12  | m                  |
| 22.57 | 3.94  | vs                 |
| 22.96 | 3.87  | w                  |
| 25.45 | 3.50  | w                  |
| 27.00 | 3.30  | w                  |
| 29.00 | 3.08  | w                  |
| 29.65 | 3.01  | m                  |
| 30.60 | 2.92  | w                  |

When the only elements which are present in the framework are Sn and Si, the molecular sieve can either have the zeolite beta structure or be amorphous with short range order. The amorphous composition has the characteristics of the material described in U.S. Pat. No. 3,556,725.

As synthesized, the molecular sieves of this invention will contain some of the organic templating agent and fluoride ions in the pores of the sieve. In order to activate the zeolite, i.e., active for adsorption or catalytic reactions, it is necessary to remove the organic template and fluoride. This is generally accomplished by calcining the molecular sieve at a temperature of about 300° C. to about 1000° C. for a time sufficient to remove substantially all the organic template and fluoride which usually is about 1 to about 10 hrs.

The molecular sieves described above are useful as catalysts for the reduction of organic oxygenates selected from ketones, aldehydes and mixtures thereof to alcohols. Examples of ketones which can be used in the instant process include without limitation alkyl ketones, cyclic ketones, alkyl substituted cyclic ketones, aryl ketones and alkyl aryl ketones. Specific examples include but are not limited to acetone, 2-butanone, cyclopentanone, cyclohexanone, alkyl, di-alkyl and tri-alkyl cyclohexanone, cyclohexenone, alkyl, di-alkyl and tri-alkyl cyclohexenone, phenyl ethanone, phenyl propanone, etc. Similarly, aldehydes, which can be used in the instant process, include without limitation alkyl aldehydes, cyclic aldehydes, alkyl substituted cyclic aldehydes, aryl aldehydes and alkyl aryl aldehydes. Specific examples include but are not limited to hexanal, trans-2-hexenal, 2-cylopentyl-ethanal, 4-cyclopentyl-butanal, citral, citronellal, etc.

The process involves contacting the ketone or aldehyde with a catalyst in the presence of a primary or secondary alcohol at reduction conditions thereby reducing the ketone or aldehyde to its corresponding alcohol. The primary or secondary alcohols which act as reductants include but are not limited to isopropanol, 2-butanol, ethanol, butanol, hexanol, cyclopentanol, cyclohexanol, alkyl-cyclohexanol, alkyl cyclopentanol, phenyl-ethanol, etc. Secondary alcohols are preferred with specific examples including isopropanol, 2-butanol and cyclopentanol. As stated, the catalyst used in the instant process is the tin containing molecular sieve described above.

Reduction conditions for the instant process include a temperature of about 10° C. to about 200° C. and a pressure of about 10 kPa to about 5100 kPa. The process can be carried out in either a batch mode or a continuous mode. In a batch mode, the catalyst, oxygenate and alcohol are mixed in a suitable reactor, preferably with stirring at the desired temperature for a time (contact time) of about 0.1 to about 50 hours. Further, the ratio of alcohol to oxygenate can vary from about 0.1:1 to about 100:1 and preferably from about 1:1 to about 80:1. In a continuous mode, the catalyst can be used as a fixed bed, fluidized bed, moving bed, or any other configuration known to one of ordinary skill in the art. When a fixed bed is used, the oxygenate and alcohol can be flowed in either an upflow or downflow direction. The alcohol and oxygenate can be injected separately or can be premixed and then injected into the reactor. Regardless of how the reactants are introduced and the type of bed being used, the reactants are flowed through the reactor at a liquid hourly space velocity of about 0.05 to about 10 $hr^{-1}$ in order to ensure adequate contact time between the reactants and the catalyst. Finally, regardless of whether a batch or continuous process is used, the products, reactants and any formed by-products are separated by means well known in the art.

In order to more fully illustrate the invention, the following examples are set forth. It is to be understood that the examples are only by way of illustration and are not intended as an undue limitation on the broad scope of the invention as set forth in the appended claims.

EXAMPLE 1

This example illustrates the preparation of zeolite beta seeds according to Spanish patent application no. P9501552.

In a container there were dissolved 1.85 grams of $AlCl_3.6H_2O$ in 4.33 grams of water. To this solution 45.24 grams of tetraethylammonium hydroxide (TEAOH) (35% by weight aqueous solution) were added. Next, 40 grams of tetraethylorthosilicate (TEOS) were added and the mixture was stirred until the ethanol formed by the hydrolysis of TEOS was evaporated. The final composition of the gel was as follows:

$$SiO_2:0.28(TEA)_2O0:0.02Al_2O_3:6.5H_2O$$

The solution, which was obtained, was transferred to a Teflon® lined stainless steel autoclave, heated to 140° C., with stirring and reacted for 3 days. The product was recovered by centrifugation, washed with distilled water and dried at 100° C. The product was found to have the structure of zeolite beta with a crystallinity of about 90%.

The zeolite beta sample of the previous paragraph was dealuminated by treating 1 gram of the as-synthesized zeolite with 60 grams of $HNO_3$ (60 wt. %) at 80° C. for 24 hours. The solid was recovered by filtration, washed with distilled water and dried at 100° C. The crystallinity of this product zeolite was found to be 70% and the Si/Al ratio was determined by chemical analysis to be higher than 2,000.

EXAMPLE 2

This example illustrates the synthesis of a stannosilicate with the zeolite beta structure.

In a container there were mixed 30 grams of TEOS and 32.99 grams of TEAOH (35 wt. %). After 90 minutes, a solution of 0.43 grams of $SnCl_4.5H_2O$ (98%) in 2.75 grams of water was added and the mixture stirred until the ethanol formed by the hydrolysis of the TEOS was evaporated. To the clear solution there were added 3.2 grams of HF (48 wt. %) and a thick paste was obtained. Finally, a suspension of 0.36 grams of dealuminated zeolite beta seeds prepared as in Example 1 in 1.75 gram of water were added. The final composition of the gel is given by the following formula:

$$SiO_2:0.27(TEA)_2O0:0.008SnO_2:0.54HF:7.5H_2O$$

The paste was loaded in a Teflon®-lined stainless steel autoclave and heated to 140° C. and reacted for 11 days with stirring. After 11 days, the product was recovered by filtration and was shown by x-ray diffraction analysis to have the structure of zeolite beta and to have a crystallinity of about 95%. Chemical analysis further showed that the product contained 1.62 wt. % tin. The product was calcined at 580° C. for 3 hours and maintained its crystallinity. The empirical formula of the material on a calcined and anhydrous basis was found to be:

$$(Si_{0.992}Sn_{0.008})O_2.$$

This product was identified as sample A.

EXAMPLE 3

This example illustrates the synthesis of a stannotitanosilicate with the zeolite beta structure. In a container, 45 grams of TEOS and 0.41 grams of titaniumtetraethoxide were added and to this solution there were added 49.89 grams of TEAOH and 7.04 grams of hydrogen peroxide (35 wt. %). After 90 minutes, a solution of 0.64 grams of $SnCl_4.5H_2O$ in two grams of water were added and the mixture stirred until the ethanol formed from the hydrolysis of TEOS was evaporated. To this solution there were added 4.94 grams of HF (48 wt. %) and a thick paste was obtained. Finally, a suspension of 0.55 grams of dealuminated zeolite beta seeds (prepared as in Example 1) in 2.5 grams of water were added. The final composition of the gel is described by the following formula.

$$SiO_2:0.27(TEA)_2O0:0.008SnO_2:0.008TiO_2:0.54HF:0.33H_2O_2:7.5H_2O$$

The paste was loaded into a Teflon®-lined stainless steel autoclave and heated to 140° C. for 20 days with stirring. After this time, the product was recovered by filtration to give a product which contained silicon, tin and titanium in the framework and had the x-ray diffraction pattern of zeolite beta. The crystallinity of the product as measured from its x-ray diffraction pattern was about 95%. A portion of this sample was analyzed and showed that it contained 1.72 wt. % tin and 0.25 wt. % titanium. After calcination at 580° C. the stannotitanosilicate molecular sieve maintained its crystallinity. The empirical formula of the product on a calcined and anhydrous basis was determined to be:

$$(Si_{0.988}Sn_{0.009}Ti_{0.003})O_2.$$

This sample was identified as sample B.

EXAMPLE 4

This example illustrates the synthesis of an aluminosilicate with the zeolite Beta structure. In a container, 40 grams of TEOS and 33.3 grams of TEAOH (35%) were added. After 90 minutes, a solution of 0.41 grams of metallic aluminum in 16.78 grams of TEAOH was added and the mixture was stirred until the ethanol formed from hydrolysis of TEOS was evaporated. To this solution there were added 4.96 grams of HF (48%) and a thick paste was obtained. Finally, a suspension of 0.34 grams of zeolite Beta seeds (non-dealuminated, Si/Al=25, prepared as in example 1) in 1.3 grams of water was added. The final composition of the gel is described by the following formula:

$$SiO_2:0.31 (TEA)_2O:0.04Al_2O_3:0.62HF:7.5H_2O$$

This paste was loaded in Teflon®-lined stainless steel autoclaves and heated to 140° C. for 2 days with stirring. After this time, the product was recovered by filtration and was found to have the x-ray diffraction pattern of zeolite beta and a crystallinity of about 100%. Chemical analysis of the material showed a Si/Al ratio of 15. The product was calcined at 580° C. for 3 hours and its crystallinity was about 90%.

This product was identified as Sample C.

EXAMPLE 5

This example illustrates the synthesis of a titanosilicate with the zeolite Beta structure. In a container, 40 grams of TEOS and 1.54 grams of titaniumtetraethoxide were added and to this solution there were added 45.38 grams of TEAOH (35%) and 6.40 grams of hydrogen peroxide (35%). The mixture was stirred until the ethanol formed from the hydrolysis of TEOS was evaporated. To this solution there were added 4.50 grams of HF (48%) and a thick paste was obtained. Finally, a suspension of 0.48 grams of dealuminated zeolite Beta seeds (prepared as in example 1) in 2.3 grams of water was added. The final composition of the gel is described by the following formula:

$$SiO_2:0.28(TEA)_2O:0.035TiO_2:0.56HF:0.34H_2O_2:7.5H_2O$$

This paste was loaded in Teflon®-lined stainless steel autoclaves and heated to 140° C. for 7 days with stirring. After this time, the product was recovered by filtration to give a product which contained silicon and titanium in the framework and had the x-ray diffraction pattern of zeolite beta. The crystallinity of the product as measured from its x-ray diffraction pattern was about 100%. A portion of this sample was analyzed and showed that it contained 1.2 wt. % titanium. After calcination at 580° C. the titanosilicate molecular sieve maintained its crystallinity. The empirical formula of the product on a calcined and anhydrous basis was determined to be:

$$(Si_{0.985}Ti_{0.015})O_2.$$

This sample was identified as Sample D.

EXAMPLE 6

This example illustrates the synthesis of a titanosilicate with the MCM-41 structure. In a container, 4.74 grams of cetyltrimethylammonium bromide (CTABr) were dissolved in an alkaline solution obtained by adding 4.73 grams of tetramethylammonium hydroxide (TMAOH, 25 wt. %) to 18 grams of water. This mixture was heated at 40° C. with stirring and held there until a clear solution was obtained, then cooled to room temperature. To the solution 0.17 grams of titaniumtetraethoxide were added, the resultant mixture was stirred for 2 hours, at which time there were added 3 grams of silica (Aerosil™ 200, Degussa), and the reaction mixture stirred for one hour. The final composition of the gel is described by the following formula:

$$SiO_2:0.26CTABr:0.26TMAOH:0.015\ TiO_2:24H_2O$$

The gel was loaded into a Teflon®-lined stainless steel autoclave and heated to 100° C. for 48 hours. After this time, the product was recovered by filtration to give a product which contained silicon and titanium in the framework and had the x-ray diffraction pattern of MCM-41. A portion of this sample was analyzed and showed that it contained 1.2 wt. % titanium.

The occluded organic material was extracted by treating 1 gram of the Ti-MCM-41 product with 50 grams of a 0.05 M ethanolic solution of $H_2SO_4$ at 70° C. for 1 hour. The product was recovered by filtration and then washed with ethanol. A second extraction was then performed using an azeotropic mixture of n-heptane and ethanol with HCl 0.15 M at 80° C. for 4 hours. The product was recovered by filtration and washed with an n-heptane-ethanol mixture.

The resulting Ti-MCM-41 product was submitted to the following surface silylation process: 1 gram of Ti-MCM-41 was outgassed at 300° C. for 2 hours. Then, 10 grams of a solution containing 0.4 grams of hexamethyldisilazane in toluene was added under Argon. The resulting mixture was refluxed under Argon atmosphere at 120° C. for 2 hours. The silylated sample was recovered by filtration and washing with toluene.

This sample was identified as Sample E.

EXAMPLE 7

Samples A to E were tested for the selective reduction of cyclohexanone as follows. In a 10 ml round bottom flask there were added 125 mg of the selected catalyst, 1 mmole of cyclohexanone and 80 mmole of isopropanol. The flask was immersed in a thermostated bath, fitted with a condenser thermometer and a magnetic stirrer and heated to 85° C. After one hour at 85° C., a sample was removed and analyzed by GC-MS. The conversion of cyclohexanone along with the selectivity to cyclohexanol are presented in Table 1.

TABLE 1

Selective Reduction of Cyclohexanone by Various Catalysts

| Catalyst I.D. | Cyclohexanone Conversion (%) | Cyclohexanol Selectivity (%) |
|---|---|---|
| A (Sn-β) | 93.8 | 100 |
| B (Ti/Sn-β) | 93.8 | 100 |
| C (Al-β) | 44.6 | 74.6 |
| D (Ti-β(F)) | 5.5 | 92.8 |
| E | 0.0 | 0.0 |

EXAMPLE 8

A Sn-beta molecular sieve prepared as in example 2 and having nominally 1.62% Sn was tested for the reduction of cyclohexanone using various alcohols. The reactions were carried out at 100° C. (except isopropanol was at 85° C.) using 1 mmole of cyclohexanone, 80 mmole of alcohol, 75 mg of catalyst. The results presented in Table 2 are after reaction for six hours.

TABLE 2

Effect of Various Alcohols on Cyclohexanone Reduction

| Alcohol | Cyclohexanone Conversion (%) | Selectivity To Cyclohexanol (%) |
|---|---|---|
| iso-propanol[1] | 93.8 | 100 |
| 2-butanol | 96.6 | 88.6 |
| Cyclopentanol | 84.7 | 90.8 |
| methyl-cyclohexanol | 32 | 74.4 |

[1]reacted at 85° C.

EXAMPLE 9

The effect of the ratio of iso-propanol to cyclohexanone was determined using the catalyst of example 8. The reaction conditions were 100° C., 75 mg of catalyst and various ratios of isopropanol/cyclohexanone. The results after 1 and 6 hours of reaction are shown in Table 3.

TABLE 3

Effect of Iso-Propanol/Cyclohexanone on Cyclohexanone Conversion

| Iso-Propanol: Cyclohexanone Ratio (mmole) | Cyclohexanone Conversion (%) 1 hr. | 6 hr. | Selectivity to Cyclohexanol |
|---|---|---|---|
| 80/1 | 95.8 | 96.0 | 100 |
| 6/1 | 39.3 | 89.7 | 99.2 |
| 4/1 | 17.9 | 66.0 | 99.5 |
| 2/1 | 0.5 | 22.3 | 100 |
| 48/0.6 | 91.0 | 95.4 | 100 |
| 37/6 | 53.5 | 95.7 | 99.0 |
| 37/9 | 63.2 | 97.5 | 99.8 |
| 37/18 | 18.0 | 84.8 | 99.8 |

EXAMPLE 10

The ability of the Sn-beta catalyst of example 8 to reduce various ketones was tested at 100° C. (or 85° C.) using 0.6 mmole of ketone, 48 mmole of alcohol and 75 mg of catalyst and the results after 6 hours of reaction are presented in Table 4. The reactions with iso-propanol were carried out at 85° while those with 2-butanol were carried out at 100° C.

TABLE 4

Reduction of Various Ketones Using a Sn-beta Catalyst

| Ketone | Alcohol | % Conversion (Ketone) | Alcohol Selectivity (Cis/Trans) % |
|---|---|---|---|
| Cyclohexanone | Isopropanol | 96.8 | 100 |
|  | 2-butanol | 96.6 | 100 |
| 4-methyl-cyclohexanone | Iso-propanol | 95.8 | 100/0 |
|  | 2-butanol | 96.5 | 100/0 |
| 4-t-butyl-cyclohexanone | Isopropanol | 97.3 | 99/0.5 |
|  | 2-butanol | 97.2 | 96/1.5 |
| 2-methyl cyclohexanone | 2-butanol | 74.0 | 50/45.4 |
| 2,6 dimethyl-cyclohexanone | 2-butanol | 21.0 | 94 |
| 2-isopropyl-5-methyl-cyclohexanone (Mentona) | 2-butanol | 5.0 | 89 |
| cyclohexenone | 2-butanol | 28.0 | 82 |
| 3,5,5-trimethyl-cyclohexanone | 2-butanol | 80 | 53 |

We claim as our invention:

1. A process for the reduction of organic oxygenates selected from the group consisting of ketones, aldehydes and mixtures thereof comprising contacting the oxygenate with a secondary or primary alcohol and a catalyst at reduction conditions, thereby reducing the oxygenate to its corresponding alcohol, the catalyst comprising a molecular sieve having an empirical formula on a calcined and anhydrous basis of:

$$(M_w Sn_x Ti_y Si_{1-x-y-z} Ge_z)O_2$$

where M is a metal having a +3 valence, "w" is the mole fraction of M and varies from zero to about 2x, "x" is the mole fraction of tin and varies from about 0.001 to about 0.1, "y" is the mole fraction of titanium and varies from zero to about 0.1 and "z" is the mole fraction of germanium and varies from zero to less than about 0.08 and characterized in that the composition has the characteristic x-ray diffraction pattern of zeolite beta, and when "w", "y" and "z" are all zero, then the molecular sieve is amorphous with short range order or has the characteristic x-ray diffraction pattern of zeolite beta.

2. The process of claim 1 where M is selected from the group consisting of aluminum, boron, gallium, and iron.

3. The process of claim 2 where M is aluminum.

4. The process of claim 1 where "y" has a value of zero.

5. The process of claim 1 where "z" has a value of zero.

6. The process of claim 1 where both "y" and "z" have a value of zero.

7. The process of claim 1 where "w", "y" and "z" have a value of zero.

8. The process of claim 1 where the process is carried out in a batch mode with a contact time of about 0.1 to about 50 hours.

9. The process of claim 1 where the process is carried out in a continuous mode at a liquid hourly space velocity of about 0.05 to about 10 hr$^{-1}$.

10. The process of claim 1 where the reduction conditions include a temperature of about 10° C. to about 200° C., a pressure of about 10 kPa to about 5100 kPa, and a contact time of about 0.1 to about 50 hours.

11. The process of claim 1 where the ratio of secondary alcohol to oxygenate varies from about 0.1 to about 100.

12. The process of claim 1 where the oxygenate is a ketone selected from the group consisting of acetone, 2-butanone, cyclopentanone, cyclohexanone, alkyl, di-alkyl and tri-alkyl cyclohexanone, cyclohexenone, alkyl, di-alkyl and tri-alkyl cyclohexenone, phenyl-ethanone and phenyl-propanone.

13. The process of claim 1 where the oxygenate is an aldehyde selected from the group consisting of trans-2-hexenal, hexanal, 2-cyclopentyl-ethanal, 4-cyclopentyl-butanal, citral and citronellal.

14. The process of claim 1 where the alcohol is selected from the group consisting of isopropanol, 2-butanol, ethanol, butanol, hexanol, cyclopentanol, cyclohexanol, alkyl-cyclopentanol, cyclohexanol, and phenyl-ethanol.

15. The process of claim 14 where the alcohol is selected from the group consisting of isopropanol, 2-butanol and cyclopentanol.

* * * * *